United States Patent
Quintero Padron et al.

(10) Patent No.: US 11,798,690 B2
(45) Date of Patent: Oct. 24, 2023

(54) METHOD OF USING MEDICAL DATA RELATED TO PATIENTS SUFFERING A GIVEN DISEASE

(71) Applicant: Atos Spain SA, Madrid (ES)

(72) Inventors: Ana Maria Quintero Padron, Santa Cruz de Tenerife (ES); Blanca Jordan Rodriguez, Madrid (ES); Carlos Cavero Barca, Madrid (ES); Manuel Marcelino Perez Perez, Madrid (ES)

(73) Assignee: BULL SAS, Les Clayes sous Bois (FR)

( * ) Notice: Subject to any disclaimer, the term of this patent is extended or adjusted under 35 U.S.C. 154(b) by 251 days.

(21) Appl. No.: 16/957,986

(22) PCT Filed: Dec. 28, 2018

(86) PCT No.: PCT/EP2018/097135
§ 371 (c)(1),
(2) Date: Jun. 25, 2020

(87) PCT Pub. No.: WO2019/129884
PCT Pub. Date: Jul. 4, 2019

(65) Prior Publication Data
US 2020/0335225 A1 Oct. 22, 2020

(30) Foreign Application Priority Data
Dec. 29, 2017 (EP) .................................. 17382922

(51) Int. Cl.
*G16H 50/70* (2018.01)
*G16H 50/50* (2018.01)
(Continued)

(52) U.S. Cl.
CPC ............. *G16H 50/70* (2018.01); *G16H 10/60* (2018.01); *G16H 20/00* (2018.01); *G16H 50/20* (2018.01); *G16H 50/50* (2018.01)

(58) Field of Classification Search
CPC ........ G16H 10/60; G16H 20/00; G16H 50/70; G16H 50/50; G16H 50/20
(Continued)

(56) References Cited

U.S. PATENT DOCUMENTS

2002/0128860 A1   9/2002 Leveque et al.
2007/0055552 A1* 3/2007 St. Clair ................. G16H 50/20
                                                             705/3
(Continued)

FOREIGN PATENT DOCUMENTS

EP      3 255 573 A1     12/2017
EP      3255573 A1  *   12/2017 ............. G06F 19/00
WO    WO-2015195741 A1 * 12/2015 ............ G06F 19/322

OTHER PUBLICATIONS

Raghupathi and Raghupathi; Big data analytics in healthcare: promise and potential; Health Information Science and Systems 2014, 2:3; http://www.hissjournal.com/content/2/1/3 (Year: 2014).*
(Continued)

*Primary Examiner* — Hiep V Nguyen
(74) *Attorney, Agent, or Firm* — MEAGHER EMANUEL LAKS GOLDBERG & LIAO, LLP

(57) ABSTRACT

This invention relates to a method of using medical data related to patients suffering a given disease, comprising: a phase of gathering (6) medical data related to patients suffering said given disease, from different hospital databases (65 to 68) storing under different data formats said medical data within non-anonymized files, a phase of storing, in a big data database (1), said gathered medical data, anonymized and in a single standardized format, a phase of using (7, 8) said big data database (1): by performing big data processing functions (21, 22) as well as by performing simple raw data extraction (23) from said big data database and direct visualization (24) of said extracted raw data, to generate one or more global rules governing categories of (Continued)

patients suffering said given disease as well as to improve personal medical care for a specific patient suffering said given disease.

20 Claims, 1 Drawing Sheet

(51) Int. Cl.
　　*G16H 10/60*　　(2018.01)
　　*G16H 50/20*　　(2018.01)
　　*G16H 20/00*　　(2018.01)
(58) Field of Classification Search
　　USPC .............................................................. 705/2
　　See application file for complete search history.

(56) References Cited

U.S. PATENT DOCUMENTS

| | | | | |
|---|---|---|---|---|
| 2014/0257047 | A1* | 9/2014 | Sillay | H04L 63/10 |
| | | | | 600/595 |
| 2014/0283097 | A1* | 9/2014 | Allen | G06F 21/6254 |
| | | | | 726/26 |
| 2017/0109475 | A1* | 4/2017 | Kaditz | G16H 50/80 |
| 2017/0357760 | A1* | 12/2017 | Han | G06N 20/00 |

OTHER PUBLICATIONS

Brito-Zerón, P. et al., "Influence of geolocation and ethnicity on the phenotypic expression of primary Sjögren's syndrome at diagnosis in 8310 patients: a cross-sectional study from the Big Data Sjögren Project Consortium," Annals of the Rheumatic Diseases, vol. 76, No. 6, dated Jun. 13, 2017, DOI: 10.1136/annrheumdis-2016-209952, pp. 1042-1050. [Only abstract disclosed, remainder of reference to be disclosed when available].

Duke, J. et al. "Open-Source Big Data Analytics in Healthcare," Observational Health Data Sciences and Informatics, MedInfo 2015, dated Jan. 1, 2015, Retrieved from the Internet: URL: www.ohdsi.org/medinfo-2015-tutorial, pp. 1-69.

"Home > Data Standardization," Observational Health Data Sciences and Informatics, Retrieved from the Internet: URL: https://www.ohdsi.org/data-standardization/, on Jun. 9, 2020, pp. 1-5.

Marcos, C. et al., "Solving the interoperability challenge of a distributed complex patient guidance system: a data integrator based on HL7's Virtual Medical Record standard," Journal of the American Medical Informatics Association, vol. 22, Issue 3, first published online on Apr. 16, 2015, DOI: 10.1093/jamia/ocv003, pp. 587-599.

International Search Report of the International Searching Authority for PCT/EP2018/097135 dated Apr. 9, 2019.

* cited by examiner

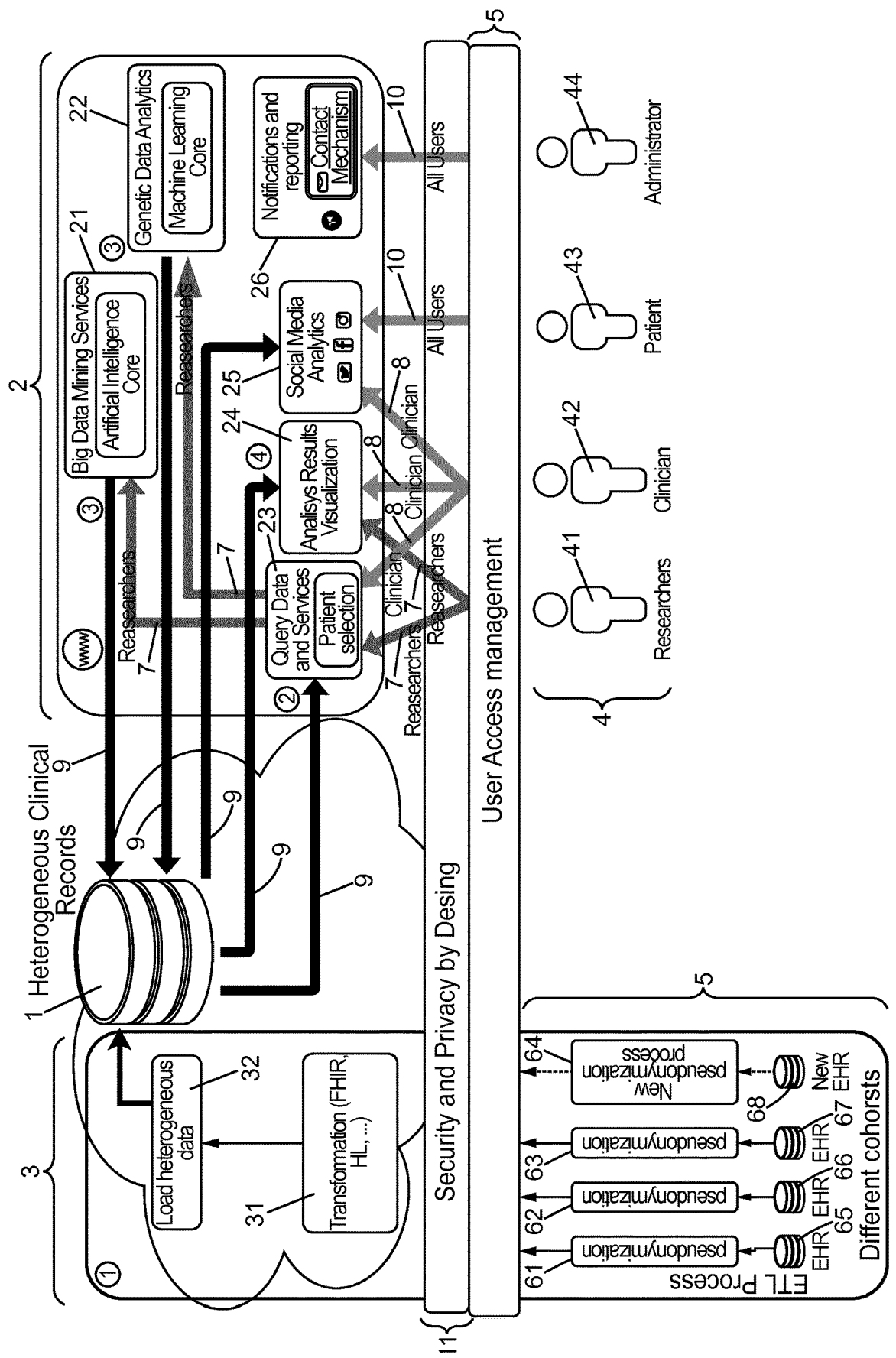

METHOD OF USING MEDICAL DATA RELATED TO PATIENTS SUFFERING A GIVEN DISEASE

FIELD OF THE INVENTION

The invention relates to the field of methods of using medical data related to patients suffering from a given disease. These methods try and help different people to get at medical information related to this disease, preferably relevant and up to date, but this is not straightforward.

BACKGROUND OF THE INVENTION

According to a prior art, when any user category wants to access to any data related to a given disease, either in order to fight this disease and to improve knowledge about this disease or in order to take advantage of most advanced existing knowledge and relevant to a specific patient to improve health of this specific patient, this user category has to consult many medical data repositories in many locations built in many different structures.

This way, this user category has but little chance to get at the right data and to make the best use of it, but for devoting a huge amount of energy and time, hardly feasible in practice.

Therefore, most often this user category gets at a far less efficient knowledge than possible or than required, leading to poor efficiency with respect to disease fighting.

Besides, when another user category wants to get at information related to this same disease, the way of searching discovered by the previous user category cannot be copied, and searching has to be made again from scratch, because of their respective different requirements.

SUMMARY OF THE INVENTION

The object of the present invention is to alleviate at least partly the above mentioned drawbacks.

To fight a disease, either on a global scale by determining the causes of this disease among a population or on an individual scale by improving personal medical care for a specific patient suffering this disease, over time, a huge number of data has become available.

However, said numerous data are distributed at different locations, stored under different ways, governed by different privacy legal requirements.

Besides, different types of people, researchers or clinicians, have very different knowledge about and ways to use all of or simply parts of this huge number of data.

As a result, getting at the right data, in the right way, for the right user, in a reasonable amount of time, is either not achievable or can only be achieved by devoting large manual work.

Therefore, often, good opportunities to fight a disease, either globally or individually, are missed, what is detrimental to public health.

The invention proposes a method of using available medical data related to patients suffering a given disease, in a more efficient and less time consuming way, despite all previously listed difficulties, to better fight a disease, either globally or individually.

More particularly, the invention aims at providing for a method of using available medical data related to patients suffering a given disease, which helps any user category at somewhat improving, in one or more respects, his goal of getting at the right data, in the right way, in a reasonable amount of time, without devoting large manual work to this task.

This object is achieved with a method of using medical data related to patients suffering a given disease, comprising: a phase of gathering medical data related to patients suffering said given disease, from different hospital databases storing under different data formats said medical data within non-anonymized files, a phase of storing, in a big data database, said gathered medical data, anonymized and in a single standardized format, a phase of using either of first or second modes each performing: a step of selection of a category of patients, a step of treatment of said stored medical data related to said selected category of patients, a step of result generation, in said first mode, said patients category is a large population of patients at a given time, said treatment uses big data processing functions, said generated result is one or more global rules governing said selected large population suffering said given disease, in said second mode, said patients category is a limited group of patients evolving over time, said treatment is mainly reduced to a simple raw data extraction from said big data database and to a direct visualization of said extracted raw data, said generated result is improvement of personal medical care for a specific patient suffering said given disease, a large population of patients being at least 100 times larger than a limited group of patients, preferably at least 1000 times larger, more preferably at least 10000 times larger.

This object is also at least partly achieved with a method of using medical data related to patients suffering a given disease, comprising: a phase of gathering medical data related to patients suffering said given disease, from different hospital databases storing under different data formats said medical data within non-anonymized files, a phase of storing, in a big data database, said gathered medical data, anonymized and in a single standardized format, a phase of using either of first or second modes: said first mode, using big data processing functions over a large population of patients at a given time, to generate one or more global rules governing said large population of patients suffering said given disease, said second mode, being mainly reduced to a simple raw data extraction from said big data database and to a direct visualization of said extracted raw data, over a limited group of patients evolving over time, to generate an improvement of personal medical care for a specific patient suffering said given disease, a large population of patients being at least 100 times larger than a limited group of patients, preferably at least 1000 times larger, more preferably at least 10000 times larger.

This object is also at least partly achieved with a method of using medical data related to patients suffering a given disease, comprising: a phase of gathering medical data related to patients suffering said given disease, from different hospital databases storing under different data formats said medical data within non-anonymized files, a phase of storing, in a big data database, said gathered medical data, anonymized and in a single standardized format, a phase of using said big data database: by using big data processing functions and/or by performing simple raw data extraction from said big data database and direct visualization of said extracted raw data, over a large population of patients and/or over a limited group of patients, said large population being larger than said limited group of patients, at a given time and/or evolving over time, to generate one or more global rules governing categories of patients suffering said given disease and/or to improve personal medical care for a specific patient suffering said given disease.

This object is also at least partly achieved with a method of using medical data related to patients suffering a given disease, comprising: a phase of gathering medical data related to patients suffering said given disease, from different hospital databases storing under different data formats said medical data within non-anonymized files, a phase of storing, in a big data database, said gathered medical data, anonymized and in a single standardized format, a phase of using said big data database: by performing big data processing functions as well as by performing simple raw data extraction from said big data database and direct visualization of said extracted raw data, to generate one or more global rules governing categories of patients suffering said given disease as well as to improve personal medical care for a specific patient suffering said given disease.

This object is still achieved with an architecture of network managing medical data related to patients suffering a given disease, comprising: different hospital databases storing under different data formats said medical data within nominative files, a gathering system adapted to gather medical data related to patients suffering said given disease, from said different hospital databases, a big data database adapted to store, said gathered medical data, anonymized and in a single standardized format, a processing system adapted to process said big data database: by performing big data processing functions as well as by performing simple raw data extraction from said big data database and direct visualization of said extracted raw data, to generate one or more global rules governing categories of patients suffering said given disease as well as to improve personal medical care for a specific patient suffering said given disease.

Preferred embodiments comprise one or more of the following features, which can be taken separately or together, either in partial combination or in full combination, with any of preceding objects of the invention.

Preferably, between said phase of gathering and said phase of storing, there is a phase of transforming said gathered medical data into a common and homogeneous model in which medical data from different sources are first transformed and later on stored under said single standardized format.

Moreover, having harmonized and standardized the medical data, improves the efficiency of big data processing functions, thereby improving again the efficiency of the method of using medical data related to patients suffering a given disease.

Preferably, said one or more global rules governing categories of patients suffering said given disease deal with determining one or more causes of said given disease, said categories corresponding to sub-groups among patients suffering said given disease.

This is a more efficient way to improve global disease fighting.

Preferably, said direct visualization of said extracted raw data improves a diagnosis dedicated to specific patient suffering said given disease performed by a medical expert thereby improving personal medical care for said specific patient suffering said given disease.

This is a more efficient way to improve individual disease fighting.

Preferably, performing big data processing functions include performing big data mining services, preferably based on an artificial intelligence core, and/or performing genomics data analytics, preferably based on a machine learning code.

Hence, most advanced big data processing functions are used.

Preferably, access to said first mode will be restricted to a first category of users which are researchers, access to said second mode will be restricted to a second category of users which are clinicians, a same person may belong to both said first and second categories.

Hence, only useful and relevant parts of big data database and associated functionalities will be made accessible for each corresponding user category.

Preferably, said different data formats from said different hospital databases are specific and/or proprietary Electronic Health Record formats.

This makes the homogenization effort performed by the method according to the invention all the more useful.

Preferably, there is a third category of users who are patients and who can access neither first mode nor second mode but who can access a third mode by: consulting publications made by users of said first mode, and/or providing feedback to the big data database based on their own experience.

Hence, only useful and relevant parts of big data database and associated functionalities will be made accessible for each corresponding user category.

Preferably, there is an administrator who gives users access to said first mode and/or to said second mode and/or to said third mode, depending on their respective status of researcher and/or clinician and/or patient.

This specific access control is useful, given the big size of the big data database and the high number of users, moreover belonging to several different user categories.

Preferably, said gathered medical data not only integrate medical data as such but also metadata related to said medical data.

This makes big data processing functions more efficient.

Preferably, said big data processing functions include big data mining services which include one or more preprocessing functions and/or one or more feature selection functions and/or one or more feature creation functions and/or one or more clustering functions and/or one or more prediction analysis functions and/or one or more association analysis functions and/or one or more prediction model creating functions and/or one or more scoring system creating functions and/or one or more multi parametric analysis functions and/or one or more machine learning functions.

Hence, most advanced big data processing functions are used.

Preferably, said big data processing functions include genomics data analytics which include one or more disease genomics roots identifying functions and/or one or more genomics data association pattern(s) analyzing functions and/or one or more genomics data association pattern(s) visualizing functions and/or one or more haplotype analysis functions and/or one or more association test(s) functions and/or one or more clustering functions and/or one or more prediction analysis functions and/or one or more association analysis functions.

Hence, most advanced big data processing functions are used.

Preferably, said big data processing functions include data and results visualization functions which include one or more filtering functions and/or one or more clustering functions and/or one or more classifying functions and/or one or more custom cohort(s) iteratively building functions.

Hence, most advanced big data processing functions are used.

Preferably, said using phase includes one or more steps of communication between users allowing for real time suggestion sending and/or real time question sending.

This is a simple way to further enrich the big data database which is already a huge one.

Preferably, said using phase includes one or more steps of regular reporting about medical data use towards said different hospital databases.

This leads to a win-win benefit between on the one side the big data database and on the other side the hospitals. Indeed, hospitals, which have helped to build the big data database, will also benefit from the medical results and improvements obtained by further processing of this big data database.

Preferably, said using phase includes one or more social media analytics functions displaying, into social media, public posts made by users of said big data database.

This allows for real time cooperation between the big data database and the high number of potential users, what benefits to everybody.

Preferably, said public posts are embedded within a platform integrated in said big data database.

This way, public posts are simpler to be managed.

Preferably, said public posts are made accessible via Facebook post and/or via Twitter post. Facebook and Twitter are registered trademarks.

Hence, interaction with the potential community of users is further enlarged.

Preferably, said using phase includes one or more public health policies impact assessing functions which combine and/or match and/or model said results generated by said big data processing functions together with public health statistics data.

This cooperation between this big data database and the public health available data further increases notably the whole set of data made available through this big data database thereby further improving its efficiency.

Preferably, said big data database is integrated in a secure cloud infrastructure.

Hence, security risk management of a huge amount of very sensitive data is improved.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 shows an example of a global architecture performing the method of using medical data related to patients suffering a given disease according to an embodiment of the invention.

DETAILED DESCRIPTION OF THE INVENTION

FIG. 1 shows an example of a global architecture performing the method of using medical data related to patients suffering a given disease according to an embodiment of the invention.

A big data database 1 centralizes all available medical data related to patients suffering a given disease. This big data database stores originally non-anonymized medical data coming from heterogeneous clinical records into a single standardized format and under an anonymized form.

This big data database is fed by a group of different hospital databases 65, 66 and 67 through a gathering phase 6. Those hospital databases of different and proprietary formats perform respective steps 61, 62 and 63, of medical data anonymization, before sending anonymized medical data to preprocessing stage 3 of the big data database 1. This anonymization can be preferably a pseudonymization: only the patient name and address are withdrawn, all other personal data are kept: it is theoretically not impossible to find back patient's identity by crossing many information, but it is far beyond the possibilities of usual users.

Preprocessing stage 3 performs a first preprocessing step 31 of medical data transformation, like FHIR or HL for instance, and then a second preprocessing step of loading the heterogeneous medical data and transforming them into a single standardized format, so as to gather and store medical data related to patients suffering from a same given disease, within anonymized and standardized files in the big data database 1.

In case a new hospital database 68 wants to include its medical data related to this given disease, later on, into this already existing big data database 1, it should only anonymize these medical data in an anonymization step 64, before sending them similarly to preprocessing stage 3.

At the end of preprocessing stage 3, each medical data set has been transformed into a common "HarmonicSS" data structure. This "HarmonicSS" data structure includes integrated cohorts which follow a specific structural model, for example a Database Schema or an XML Schema.

The medical data elements in the medical data sets which are included in the "HarmonicSS" integrated cohorts are also accompanied by metadata, which metadata give a clear insight of the other medical data elements they are linked with, such as its purpose, any specific methods it has been based on, definition, if required, etc. . . . . This preprocessing stage 3 module is closely related to governance framework.

The processing stage 2 includes big data processing functions among which big data mining services 21 based on artificial intelligence core as well as genomics data analytics 22 based on machine learning core. Both big data mining services 21 and genomics data analytics 22 can process simultaneously a huge number of medical data stored in the big data database 1.

The role of the big data mining services 21 is to offer, to the users of the platform, tools and algorithms to analyze the medical data integrated cohorts. A series of tools is offered for analytics, ranging from preprocessing, feature selection and creation, clustering, prediction and association analysis. The requirements provided by the users are thereby covered. There are provided both a learning phase, for example to create a model of prediction or to create a scoring system, but also the possibility to deploy this prediction model. Included algorithms and tools take into account the time dimension, since longitudinal data will be available in the integrated cohorts.

Genetic data analytics function 22 is performed by a module which makes users to understand what causes a specific disease, for example Sjögren's syndrome, and to further identify the genetic roots of this specific disease. Subsequently, the underlying molecular mechanisms related to this specific disease can be elucidated and new ways to treat this specific disease may hopefully be thereby unveiled. The genetic data analytics function 22 offers to the users of the platform, tools and services to further analyze the acquired genetic data. Bioinformatics software will be applied with reference to the requirements provided by the users in order to analyze and visualize patterns of association in genetic data. The molecular mechanisms underlying this specific disease can be elucidated through haplotype analysis and association tests, and the risk variants that predispose to this specific disease may be further identified. In addition, tools are employed for further analyzing the genetic analysis results, ranging from clustering and association to prediction.

This processing stage 2 also includes other functions, like a data and services query function 23 which includes patient category selection and which among others allows for simple raw data extraction, like an analysis results visualization function 24 which among others allows for a direct visualization, for instance on a computer screen, of said extracted raw data, a social media analytics function 25 which allows among others for publication of new information related to this given disease coming from work and experimentation of researchers 41 and clinicians 42, and a notifications and reporting function 26 which allows for users enlargement and real time interaction between users for example through chatting.

The analysis results visualization function 24 allows researchers 41 and clinicians 42, to see, filter and compare, medical data and analysis results. The module corresponding to this analysis results visualization function 24 is accessible by authorized actors, which are researchers 41 and clinicians 42, and it is preferably available 24 hours a day, through web access, but via secure access (https). This module displays suitable analysis results previously obtained using the big data mining services 21 and the genomics or genetic data analytics 22. This module provides an interactive tool to view and iteratively build custom cohorts using filtering methods, assisted by visual and statistical aids. Results from other modules can be integrated. Such results may include clustering data, for example for the identification of new cohorts, or classification and/or prediction results, for the enrichment of the patient medical data set. Conversely, results obtained by this module, including custom cohort definitions, can be used by other modules in the same way.

The social media analytics function 25 includes a social media analytics module as well as a health policies impact assessment module.

This social media analytics module displays all public posts in social media related to a specific disease, for example related to "Sjögren's syndrome", for example on Facebook (registered trademark) and or on Twitter (registered trademark). This social media analytics module is accessible for researchers 41 and clinicians 42 and allows the user to include "free text" in order to refine the list of posts by adding time, location, symptoms, therapies, etc . . . , but only if the public post contains this information. Embedded Posts are a simple way to put public posts, by a page or by a person, into "HarmonicSS" platform. Only public posts are embedded. To access Facebook (registered trademark) post, an application programming interface is used to get data out of, and put data into, Facebook's platform (registered trademark). A low-level HTTP-based application programming interface is used to programmatically query data, post new stories, manage ads, upload photos, and perform other usual tasks that an application programming interface may usually implement. To access to Twitter (registered trademark) post, there is not a dedicated functionality, so this is worked around, for example, by using "HarmonicSS" Twitter (registered trademark) user and get mentions #hashtags, like #Sjögren for example.

The health policies impact assessment module performs critical assessments of various management intervention scenarios. This health policies impact assessment module uses a consistent estimation of various parameters not only related to patients themselves, but also to social and financial factors. The task of this health policies impact assessment module includes assessing the impact of the public health policies scenarios based on the "big picture" of the available medical data obtained using a variety of techniques such as big data mining, social media analytics, genomics or genetics analytics and visual analytics. The impact assessment of the developed health policies services in healthcare systems, financial figures and society are assessed by combining, matching and modelling the input data from the "HarmonicSS" modules with specific output data obtained from health statistics data, for example "Linked Eurostat", based on a customized version of the European Union health systems impact assessment tool. A panel of clinical experts may also assist the impact assessment and review process.

The notifications and reporting function 26 includes a notification module and a reporting module.

This notification module allows users to send suggestions and questions to another user. This module allows all users to get in contact with other users in order to make a question, suggestion, regarding the published medical data. Researchers 41 may want to contact the medical data provider to discuss interesting properties of these medical data, or to contemplate future collaborations. All notifications are displayed in real time on a main interface, once the user logs into the system. This notification module provides real time medical data transfer from and to the server, so that, any time a new notification is created, the system will add this new notification to a notifications panel.

A notification contains: a date time of creation which is automatically generated, a user name of creation which corresponds to the logged user, a user name of receiver which corresponds to the receiver user, a notification text which can be an enriched text allowing bold, italic, external and internal link, a read flag to know if a user has read or not one specific notification, any unread notification being highlighted. In next TABLE 1, there is an example of notification format:

TABLE 1

2201/17 12:11from username1: HarmonicSS report date time generated, click here to access and download it,
0201/17 01:00 from username3: Notification 4
5/02/17 09:00 from username2: Notification 5

The reporting module keeps medical data providers regularly informed about their medical data usage. This reporting module creates a regular PDF report, for example each day but the period may also be configured, and sends it to its data providers, taking into account data usage in a big data analysis module. This report includes information such as: general information, period date of the report, data time of generation, specific details, name of the person who accessed their medical data sets, date of consulting, number of medical data set requests in the reporting period. This reporting module collects usage of medical data and generates the PDF report as well as a notification thereby using notification module to inform the user. An example of a reporting notification by notification module is given in next TABLE 2.

TABLE 2

25/01/17 12:00 from username1: Notice that . . .
2201/7 12:11from username1: HarmonicSS report data time generated, click here to access and download it The group of users 4 includes researchers 41, clinicians 42 which are often medical doctors, patients 43 and an administrator 44. The respective status of researchers 41, clinicians 42 and patients 43, are given by the administrator 44 through user access management 5. The respective status of researchers 41, clinicians 42 and patients 43, allow these respective users to different function access. A same person may gain different types of status, for example researcher 41 and clinician 42 simultaneously, if he deserves it.

The user access management 5 module manages the access to HarmonicSS platform for authorized users in a secure way. Only authorized users may access to different functionalities, depending on their role and logged level. Once logged in, each level should unlock a specific set of functionalities; no user can exploit a "stronger" functionality using a "weaker" identity.

Researchers 41, have researcher access 7 authorizing them access to big data mining services 21, genomics data analytics 22, as well as to data and services function 23 and analytics results visualization function 24. Researcher access 7 might also authorize access to social media analytics function 25 in active mode by posting new information on it, in an alternative.

Clinicians 42, have clinician access 8 authorizing them access to data and services function 23 and analytics results visualization function 24, as well as to social media analytics function 25 in active mode by posting new information on it. In an option, clinicians 42 may have access to anonymized complete patient life cycle, whereas researchers 41 may only have access to part such patient life cycle closely related to their research topic.

All users, including patients 43, researchers 41 and clinicians 42, have all user access 10, authorizing them access to social media analytics function 25 in passive mode by consulting newly posted information on it, as well as to notifications and reporting function 26.

The interaction between big data database 1 and processing stage 2 is shown by arrows 9. The big data database 1 feeds data and services function 23 and analytics results visualization function 24, as well as social media analytics function 25. The big data database 1 is consulted by big data mining services 21 and genomics data analytics 22, as well as enriched by results obtained by big data mining services 21 and genomics data analytics 22.

There is also a security and privacy 11 module. Therein, security protocols are defined and implemented for medical data at rest, medical data in transit, for authentication of users and applications and processes, for separation between data belonging to different partners, for cloud legal and regulatory issues, and for incident response. The security mechanisms for the "HarmonicSS" platform are included. Set up of the secure cloud infrastructure, repositories and platform, and privacy issues are also implemented.

There is also an audit medical data module, not represented on FIG. 1 for clarity reasons, which creates a log of all HarmonicSS data transactions through an audit trail. This enables to keep track of changes and updates made to harmonized medical data. The administrator 44 checks this information. This audit medical data module records information regarding to, who had access, through which service, at which time point.

The invention has been described with reference to preferred embodiments. However, many variations are possible within the scope of the invention.

The invention claimed is:

1. Method of using medical data related to patients suffering a given disease, comprising:
    gathering (6) medical data related to patients suffering said given disease, from different hospital databases (65 to 68) storing under different data formats said medical data within non-anonymized files,
    storing, in a big data database (1), said gathered medical data, anonymized and in a single standardized format,
    using either of first or second modes (7, 8) each performing:
        a selecting (23) of a category of patients,
        treating, using a treatment (21, 22, 23, 24), of said stored medical data related to said selected category of patients, in order to generate a result,
    in said first mode (7),
        said patients category is a first population of patients at a given time,
        said treatment uses big data processing functions (21, 22), said big data processing functions comprising big data mining services and genomics data analytics,
        said generated result is one or more global rules governing said first population suffering said given disease, said one or more global rules comprising at least one rule determining one or more causes of said given disease,
    in said second mode (8),
        said patients category is a second group of patients evolving over time, where said first group of patients is at least 100 times larger than said second group of patients,
        said treatment is mainly reduced to a simple raw data extraction (23) from said big data database (1) and to a direct visualization (24) of said extracted raw data,
        said generated result is improvement of personal medical care for a specific patient suffering said given disease.

2. Method of using medical data related to patients suffering a given disease, according to claim 1, wherein between said gathering (6) and said storing (1), the method includes transforming (3) said gathered medical data into a common and homogeneous model in which medical data from different sources are first transformed and later on stored under said single standardized format.

3. Method of using medical data related to patients suffering a given disease, according to claim 1, wherein said one or more global rules governing categories of patients suffering said given disease deal with determining one or more causes of said given disease, said categories corresponding to sub-groups among patients suffering said given disease.

4. Method of using medical data related to patients suffering a given disease, according to claim 1, wherein said direct visualization (24) of said extracted raw data improves a diagnosis dedicated to specific patient suffering said given disease performed by a medical expert thereby improving personal medical care for said specific patient suffering said given disease.

5. Method of using medical data related to patients suffering a given disease, according to claim 1, wherein performing big data processing functions (21, 22) include performing big data mining services (21), preferably based on an artificial intelligence core, and/or performing genomics data analytics (22), preferably based on a machine learning code.

6. Method of using medical data related to patients suffering a given disease, according to claim 1, wherein:
   access to said first mode (7) will be restricted to a first category of users which are researchers (41),
   access to said second mode (8) will be restricted to a second category of users which are clinicians (42),
   a same person may belong to both said first and second categories.

7. Method of using medical data related to patients suffering a given disease, according to claim 1, wherein said different data formats from said different hospital databases (65 to 68) are specific and/or proprietary Electronic Health Record formats.

8. Method of using medical data related to patients suffering a given disease, according to claim 1, wherein there is a third category of users who are patients (43) and who can access neither first mode (7) nor second mode (8) but who can access a third mode (10) by:
   consulting publications (26) made by users of said first mode (7), and/or
   providing feedback (26) to the big data database (1) based on their own experience.

9. Method of using medical data related to patients suffering a given disease, according to claim 1, wherein there is an administrator (44) who gives users access to said first mode (7) and/or to said second mode (8) and/or to said third mode (10), depending on their respective status of researcher (41) and/or clinician (42) and/or patient (43).

10. Method of using medical data related to patients suffering a given disease, according to claim 1, wherein said gathered medical data not only integrate medical data as such but also metadata related to said medical data.

11. Method of using medical data related to patients suffering a given disease, according to claim 1, wherein:
   said big data processing functions (21, 22) include big data mining services (21) which include one or more preprocessing functions and/or one or more feature selection functions and/or one or more feature creation functions and/or one or more clustering functions and/or one or more prediction analysis functions and/or one or more association analysis functions and/or one or more prediction model creating functions and/or one or more scoring system creating functions and/or one or more multi parametric analysis functions and/or one or more machine learning functions, and/or
   said big data processing functions (21, 22) include genomics data analytics (22) which include one or more disease genomics roots identifying functions and/or one or more genomics data association pattern(s) analyzing functions and/or one or more genomics data association pattern(s) visualizing functions and/or one or more haplotype analysis functions and/or one or more association test(s) functions and/or one or more clustering functions and/or one or more prediction analysis functions and/or one or more association analysis functions, and/or
   said big data processing functions (21, 22) include data and results visualization functions which include one or more filtering functions and/or one or more clustering functions and/or one or more classifying functions and/or one or more custom cohort(s) iteratively building functions.

12. Method of using medical data related to patients suffering a given disease, according to claim 1, wherein:
   said using phase (7, 8) includes one or more steps of communication between users allowing for real time suggestion sending (26) and/or real time question sending (26), and/or wherein
   said using phase (7, 8) includes one or more steps of regular reporting (26) about medical data use towards said different hospital databases (65 to 68).

13. Method of using medical data related to patients suffering a given disease, according to claim 1, wherein said using phase (7, 8) includes one or more social media analytics functions (25) displaying, into social media, public posts made by users of said big data database (1).

14. Method of using medical data related to patients suffering a given disease, according to claim 1, wherein said public posts are embedded within a platform integrated in said big data database (1).

15. Method of using medical data related to patients suffering a given disease, according to claim 1, wherein said public posts are made accessible via Facebook post and/or via Twitter post.

16. Method of using medical data related to patients suffering a given disease, according to claim 1, wherein said using phase (7, 8) includes one or more public health policies impact assessing functions which combine and/or match and/or model said results generated by said big data processing functions (21, 22) together with public health statistics data.

17. Method of using medical data related to patients suffering a given disease, according to claim 1, wherein said big data database (1) is integrated in a secure cloud infrastructure.

18. Method of using medical data related to patients suffering a given disease, comprising:
   gathering (6) medical data related to patients suffering said given disease, from different hospital databases (65 to 68) storing under different data formats said medical data within non-anonymized files,
   storing, in a big data database (1), said gathered medical data, anonymized and in a single standardized format,
   using either of first or second modes (7, 8):
      said first mode (7), using big data processing functions (21, 22) over a first population of patients at a given time, to generate one or more global rules governing said first population of patients suffering said given disease, said big data processing functions comprising big data mining services and genomics data analytics, said one or more global rules comprising at least one rule determining one or more causes of said given disease,
      said second mode (8), being mainly reduced to a simple raw data extraction (23) from said big data database and to a direct visualization (24) of said extracted raw data, over a second group of patients evolving over time, to generate an improvement of personal medical care for a specific patient suffering said given disease, where said first population of patients is at least 100 times larger than said second group of patients.

19. Method of using medical data related to patients suffering a given disease, comprising:
   gathering (6) medical data related to patients suffering said given disease, from different hospital databases (65 to 68) storing under different data formats said medical data within non-anonymized files, storing, in a big data database (1), said gathered medical data, anonymized and in a single standardized format, using (7, 8) said big data database (1):

by using big data processing functions (21, 22) and/or by performing simple raw data extraction (23) from said big data database (1) and direct visualization (24) of said extracted raw data, said big data processing functions comprising big data mining services and genomics data analytics, over a first population of patients and/or over a second group of patients, said first population being larger than said second group of patients, at a given time and/or evolving over time, to generate one or more global rules governing categories of patients suffering said given disease and/or to improve personal medical care for a specific patient suffering said given disease, said one or more global rules comprising at least one rule determining one or more causes of said given disease.

20. A system for managing medical data related to patients suffering a given disease, comprising:

different hospital databases (65 to 68) storing under different data formats said medical data within nominative files, a gathering system (6) adapted to gather medical data related to patients suffering said given disease, from said different hospital databases (65 to 68), a big data database (1) adapted to store, said gathered medical data, anonymized and in a single standardized format, a processing system (2) adapted to process said big data database (1):

by performing big data processing functions (21, 22) as well as by performing simple raw data extraction (23) from said big data database (1) and direct visualization (24) of said extracted raw data, said big data processing functions comprising big data mining services and genomics data analytics, to generate one or more global rules governing categories of patients suffering said given disease as well as to improve personal medical care for a specific patient suffering said given disease, said one or more global rules comprising at least one rule determining one or more causes of said given disease.

\* \* \* \* \*